United States Patent [19]

Pusey

[11] Patent Number: 5,047,239

[45] Date of Patent: * Sep. 10, 1991

[54] BIOLOGICAL CONTROL OF FRUIT ROT

[75] Inventor: P. Lawrence Pusey, Warner Robins, Ga.

[73] Assignee: The United States of America as represented by the Secretary of Agriculture, Washington, D.C.

[*] Notice: The portion of the term of this patent subsequent to Aug. 16, 2005 has been disclaimed.

[21] Appl. No.: 393,010

[22] Filed: Aug. 11, 1989

Related U.S. Application Data

[63] Continuation of Ser. No. 98,167, Sep. 18, 1987, abandoned, which is a continuation-in-part of Ser. No. 797,538, Nov. 13, 1985, Pat. No. 4,764,371, which is a continuation-in-part of Ser. No. 606,069, May 1, 1984, abandoned.

[51] Int. Cl.$^5$ ............................................. C12N 1/20
[52] U.S. Cl. .................................... 424/93; 435/839; 435/832; 426/310; 426/335
[58] Field of Search .................. 424/93; 435/839, 832; 426/310, 335

[56] References Cited

U.S. PATENT DOCUMENTS 4,764,371 8/1988 Pusey et al. ........................... 424/93

Primary Examiner—Douglas W. Robinson
Assistant Examiner—Jean C. Witz
Attorney, Agent, or Firm—M. Howard Silverstein; John D. Fado

[57] ABSTRACT

Preharvest peaches, postharvest apples and postharvest grapes are coated with *Bacillus subtilis* B-3 to inhibit growth of brown rot, gray mold rot and bitter rot.

5 Claims, No Drawings

BIOLOGICAL CONTROL OF FRUIT ROT

RELATED INVENTIONS

This is a continuation of Ser. No. 098,167, abandoned, which is a continuation-in-part of Ser. No. 797,538, filed Nov. 13, 1985, now U.S. Pat. No. 4,764,371, which in turn is a continuation-in-part of Ser. No. 606,069, filed May 1, 1984, now abandoned.

FIELD

This invention relates to biological control of fruit rot.

PRIOR ART

*Bacillus subtilis* strains have been shown to biologically control various diseases in plants. Some examples are set forth in above-cited U.S. Pat. No. 4,764,371.

SUMMARY

It now has been discovered that a strain of B. subtilis bacteria, on deposit as NRRL B-15813 (ARS Patent Collection, Northern Regional Research Center, 1815 University Street, Peoria, Ill. 61604), hereinafter referred to as strain B-3, effectively inhibits the growth of brown rot (*Monilinia fructicola*) on peaches when applied to preharvest peaches, effectively inhibits the growth of brown rot, gray mold rot (*Botrytis cinerea*) and bitter rot (*Glomerella cingulata*) on apples when applied to post harvest apples, and effectively inhibits the growth of gray mold rot on grapes when applied to post harvest grapes.

DETAILED DESCRIPTION

In the practice of the present invention with regard to preharvest treatment of peaches, the B-3 may be sprayed on a peach tree from a liquid suspension. In the case of post harvest treatment of apples or grapes, the B-3 may be sprayed or brushed thereon from a liquid suspension.

A typical aqueous suspension for spraying onto peaches contains about $10^7$–$10^8$ colony forming units (CFU) of B-3 per ml of aqueous carrier. The optimum concentration depends upon such factors as the volume of carrier applied to each tree (typically about a gallon per tree), and the flow rate of the suspension through the spray nozzle.

Such an aqueous suspension also may be used to spray onto post harvest apples or grapes. Alternatively, with regard to post harvest treatment, the B-3 may be combined with prior art wax-containing suspensions for application to fruits. For example, the B-3 may be incorporated into admixture with a typical water base non-paraffin wax suspension in a concentration of $10^8$–$10^9$ CFU per ml of suspension, and thereafter sprayed onto the fruit. Alternatively, the B-3 may be added to a prior art mineral oil base paraffin wax which typically is melted and then brushed onto fruit. Oil base waxes typically are applied in lower volumes than water base waxes whereby the concentration of B-3 in an oil base wax carrier should be greater than in a water base wax carrier, as will be readily apparent to those skilled in the art.

Whatever carrier is employed to apply B-3 to post harvest fruit, the optimum concentration of B-3 in the carrier will depend upon such factors as the flow rate through the spray nozzle (in the case of spray application), and the speed at which the fruit is moving past the application device.

A conventional nutrient growth medium may be employed to grow B-3 for use in the present invention. Details of such a medium are set forth in above-cited U.S. Pat. No. 4,764,371. The resultant cloudy suspension of nutrient and B-3 may be directly added to a carrier, or the B-3 may be separated from nutrient by centrifugation and then added to the carrier. Alternatively, the separated B-3 may be dried and thereafter ground into a powder for incorporation into a carrier, or stored prior to adding to a carrier.

In tests to date:

a. B-3 treatment of preharvested peaches subsequently exposed to *Monilinia fructicola* (brown rot) resulted in 1.7%–2.4% of the peaches being infected, whereas 20%–26.8% of similarly exposed untreated peaches became infected from such exposure. p b. Post harvest B-3 treatment of apples subsequently exposed to *M. fructicola* resulted in apples exhibiting fungal lesion diameters less than 1/5 of the lesion diameters on similarly exposed untreated apples after 6 days, and about ¼ of the lesion diameters on untreated apples after 11 days.

c. Post harvest B-3 treatment of apples subsequently exposed to *Botrytis cinerea* (gray mold rot) resulted in apples exhibiting fungal lesion diameters of less than 1/6 the diameter of the lesions on similarly exposed untreated apples after 6 days, and less than ½ the lesion diameters on the untreated apples after 11 days.

d. Post harvest B-3 treatment of apples subsequently exposed to *Glomerella cingulata* (bitter rot) resulted in apples exhibiting fungal lesion diameters less than 1/10 the lesion diameters on similarly exposed untreated apples after 6 days, and about 80% of the lesion diameters on the untreated apples after 11 days.

e. Post harvest B-3 treatment of grapes subsequently exposed to *B. cinerea* (gray mold rot) resulted in 7.7% of the grapes being infected, whereas 47.5% of similarly exposed untreated grapes became infected.

I claim:

1. A method of inhibiting brown rot on peaches comprising applying *Bacillus subtilis* B-3 to preharvest peaches in an amount to effectively inhibit said brown rot.

2. A method of inhibiting brown rot, gray mold rot and bitter rot on apples comprising applying *Bacillus subtilis* B-3 to postharvest apples in an amount to effectively inhibit said brown rot, gray mold rot and bitter rot.

3. A method of inhibiting gray mold rot on grapes comprising applying *Bacillus subtilis* B-3 to postharvest grapes in an amount to effectively inhibit said gray mold rot.

4. The method of claim 2 wherein said B-3 is applied in admixture with wax.

5. The method of claim 3 wherein said B-3 is applied in admixture with wax.

* * * * *